United States Patent [19]

Verma

[11] Patent Number: 4,591,573

[45] Date of Patent: May 27, 1986

[54] SENSITIVE RADIOIMMUNOASSAY USING ANTIBODY TO L-HYOSCYAMINE

[75] Inventor: Pritam S. Verma, Adelphi, Md.

[73] Assignee: The United States of America as represented by the Secretary of the Army, Washington, D.C.

[21] Appl. No.: 535,190

[22] Filed: Sep. 23, 1983

[51] Int. Cl.$^4$ .............. G01N 33/56; A61R 39/00; C07G 7/00

[52] U.S. Cl. .............................. 436/542; 424/85; 424/88; 436/543; 436/545; 436/547; 436/804; 436/815; 436/822; 530/387

[58] Field of Search ................ 436/504, 542, 543–545, 436/547, 804, 811, 815, 822; 424/85, 88; 260/112 B

[56] References Cited

PUBLICATIONS

Virtanen et al, Chemical Abstracts, 93 (1980), #230464d.

Lehtola et al, Chemical Abstracts, 97 (1982), #205286y.

Wurzburger et al, J. Pharmacol. Exp. Therapeut., vol. 203 (1977), 435–41.

*Primary Examiner*—Christine M. Nucker

*Attorney, Agent, or Firm*—John H. Raubitschek; Arthur I. Spechler; Werten F. W. Bellamy

[57] ABSTRACT

A sensitive and specific radioimmunoassay is developed for L-hyoscyamine resulting from atropine administration with which a concentration as low as 25 pg/ml using 0.1 ml of sample can be measured without the need for extraction. Specificity studies indicate that an antibody according to this invention has high specific recognition of L-hyoscyamine with only about 37% cross reaction with the D-hyoscyamine enantiomer of atropine. The antibody is produced from an immunogen having conjugated at least 42 and preferably 45 L-hyoscyamine-p-aminobenzoic acid haptenic molecules per molecule of bovine serum albumin. An antibody according to this invention can be used with a dilution titer as high as 1:2000.

13 Claims, 4 Drawing Figures

(1) <u>DIAZOCOUPLING</u>

L-HYOSCYAMINE (2) CONJUGATION TO BSA

PROCEDURE FOR THE PREPARATION OF L-HYOSCYAMINE BSA IMMUNOGEN

SENSITIVE RADIOIMMUNOASSAY USING ANTIBODY TO L-HYOSCYAMINE

BACKGROUND OF THE INVENTION

Drug Chemistry

L-hyoscyamine is one of three important alkaloids in belladonna, stramonium and hyoscyamus extracts. The other two are atropine and hyoscine(scopolamine). Many years after the isolation of L-hyoscyamine and atropine from solanaceous plant extracts, it was discovered that atropine is a racemic mixture of two enantiomers, L-hyoscyamine and D-hyoscyamine. Hence, one-half of atropine is L-hyoscyamine.

The original alkaloid formed in the plant is L-hyoscyamine. At the time of harvest little, if any, atropine is present in the plant. However, there is a tendency for the enantiomer to racemize. Hence during the process of extraction and concentration of the L-hyoscyamine, some of the alkaloid is converted to D-hyoscyamine resulting in the racemic mixture called atropine (D,L-hyoscyamine).

Enantiomers are identical in molecular weight and have identical physical and chemical properties except for their effect upon a plane of polarized light. However, in physiological action, they may be distinctly different. The physiological effects of the racemic mixture is of course equivalent to the sum total of the individual enantiomeric effects.

Drug Usage

Cholinesterase inhibitors are among the mostly deadly of chemical toxins. They are the active ingredients of "nerve gas" (sarin, soman) and of organophosphorus insecticides (parathion, malathion). Nerve-gas or insecticide poisoning causes cholinergic hyperactivity, including bradycardia, sialorrhea, bronchospasm and depolarizing neuromuscular paralysis. The antidotes are atropine and pralidoxime. Prospects of survival are enhanced if antidotes are given soon after exposure to toxin. Muscarine-like agents are the active toxins in many variety of poisonous mushrooms found in North America. Poisoning by Amanita muscaria is manifested by symptoms and signs of muscarinic hyperactivity occuring within a few hours of ingestion. Atropine is the antidote.

Combination of belladonna alkaloids with antihistamines are widely used as proprietary cold remedies. Anticholinergics are combined with salicylates, phenacetin or acetaminophen in various analgesic preparations; with methenamine, methylene blue, or phenazopyridine in "urinary-track sedatives", with amphetamines, barbiturates, cathartics, thyroid or digitalis in "diet pills", and with ergot alkaloids, caffeine, amphetamines or opiates in remedies for migraine and dysmenorrhea.

Atropine and belladonna extract have long been used therapeutically as gastrointestinal antispasmodics for the treatment of peptic ulcer, pyloric spasm, biliary dyskinesia, gastrointestinal spasticities, anesthesia, cardiac disease, other gastrointestinal disease, vertibular disorders, basal-ganglion disorders, ophthalmology and proprietary hypnosis.

Drug Toxicity

The widespread use of the belladonna alkaloids in clinical medicine is attested by the more than 600 available pharmaceuutical preparations and combinations containing atropine. While the drug may be life-saving in some of the above-mentioned situations, it has been associated with complications such as tachycardia, lethal arrhythmias and/or extension of the myocardial infarction. These adverse effects of the drug apparently attributed to elevated drug levels in a patient's blood which may have resulted from poor metabolism and/or higher doses of the drug. An effect on the central-nervous-system, however, is rarely tolerable. Toxicity is less predictable and more variable in occurance, usually observed in association with large therapeutic doses in any of the described settings without monitoring the drug in the patient. Anticholinergic central-nervous-system toxicity is observed in up to 20 percent of patients receiving these drugs for Parkinsonism which suggests that drug levels have to be monitored in patients in order to avoid toxicity.

Patients poisoned with anticholinergic drugs are flushed and have dry skin and mucous membranes, tachycardia, and widely dilated pupils that are poorly responsive to light. Those who are coherent have complained of dry mouth, thirst, or inability to focus. More often, the mental status is abnormal, fluctuating unpredictably from unresponsiveness and coma to an agitated, confused, delirious or psychotic state. Fever occurs in more than 25 percent of patients, but occasionally may reach dangerously high levels. Most of these toxic effects can easily be avoided by monitoring the drug levels in patients.

Toxicity data on frogs reveal atropine to be more toxic than L-hyoscyamine. The increased toxicity may be attributed to the convulsive death caused by the D-hyoscyamine content which is an excitant to the spinal cord and which is destroyed more slowly than the L-form. Comparative lethal data on other animals are not available.

Both atropine and L-hyoscyamine are excreted from the body in the urine, mostly unchanged. The serum or liver of some animals contains an enzyme which destroys the alkaloids, but human tolerance is unexplained on this basis.

Peripheral Action

L-hyoscyamine in its paralyzant effect on the peripheral distribution of the parasympathetic nervous system appears to be approximately twice as active as atropine and from 40 to 50 times as potent as the D-isomer. Tests on mydriasis, salivary secretion, cardiac vagal effects, intestinal strips, and the flush response bear out this conclusion as to the relative potencies.

One study of the mydriatic effects of L-hyoscyamine involved the injection of D-hyoscyamine and atropine subcutaneously into cats. Based on the amount of drug required to produce the same degree of mydriasis in the same cat, this study indicated a relative potency of 1:1/2:1/12 for L-, DL-, and D-, respectively. These samples were admittedly contaminated. In a similar experiment on mice the D-enantiomer was found to be 1/40 as potent as L-, and the DL-racemate to be slightly more than ½ as potent in causing pupil dilation. Another study confirmed the 1:½ ratio of L-hyoscyamine to atropine using mice as a model. An additional study reported on the action of L-hyoscyamine on the human eyes and stated that L-hyoscyamine sulphate, 0.25% solution, can replace a 1% solution of atropine sulphate. This suggests the potency of L-hyoscyamine and atropine to be in the ratio 1:¼.

Regarding the peripheral activities of the hyoscyamines, there is now ample evidence to support the conclusions that L-hyoscyamine is approximately twice as active as atropine when employed for peripheral parasympathetic effects; hence it is the most potent parasympathetic antispasmodic known. Additionally, the peripheral action of atropine is, within practical biological measurements, that of its levoisomer and, therefore, L-hyoscyamine may be given in half the dosage of atropine (D,L hyoscyamine). For practical purposes D-hyoscyamine is peripherally inactive having only 1/50 the activity of L-hyoscyamine. Concerning the effects of the hyoscyamines on the central nervous system, atropine is more toxic than L-hyoscyamine. The difference is caused by the D-hyoscyamine content's being an excitant to the spinal cord. The only relative potency analysis showed that D-hyoscyamine was 12 times and atropine 3 times more active that the L-isomer in this respect.

With regard to intestinal effects, it was reported that in counteracting the stimulating effects of acetylcholine on the isolated rad duodenum, L-hyoscyamine had twice the spasmolytic activity of atropine. These results were confirmed using intact rats.

Atropine was found to increase the excitability of the spinal cord in dogs in contrast to L-hyoscyamine which had no effect on it. Presumably the stimulation resulted from D-hyoscyamine, the only other active principle in atropine. All three hyoscyamines caused weakness and clumsy motility. Recovery was quickest after administration of L-hyoscyamine. Another study found that mice which received atropine became narcotized while those receiving L-hyoscyamine were not affected. A study of the effects in children found that the amount of L-hyoscyamine necessary to produce deep sleep was 3 times the amount of atropine and 12 times the amount of D-hyoscyamine.

One study concerning salivation found atropine to be ½ and the D-isomer only 1/40 as potent as the L-isomer upon administering the drug subcutaneously to dogs.

The hyoscyamines inhibit the vagus which in turn accelerates the heart rate. An investigation of the effects on pulse rate in dogs revealed the relationship to be L-, 1; DL-, ½; D-, 1/50 to 1/60 in terms of relative potency.

Another investigation concerned the flush sensitivity of approximately 70 children to whom the drugs were administered orally. Less quantities of L-hyoscyamine were needed than atropine, although 20–40 times as much D-hyoscyamine was required.

Drug Analysis

Despite the long history and well known pharmacodynamics of atropine, relatively little is known of its pharmacokinetic properties in man. The major reason for this is the lack of satisfactory analytical methods for measuring the extremely low concentrations of atropine after therapeutic doses. Currently available methods include bioassay, gas-liquid chromatography, flourometry and chlorometric techniques.

Radioimmunoassay (RIA) is recognized as a clinical laboratory method which has gained acceptance for the detection of microquantities of a multitude of compounds. A summary of radioimmunoassay procedure can be obtained, for example, from Stites et al., *Basic % Clinical Immunology*, 4th Edition (1982), Lange Medical Publications, Los Altos, Calif., pp 347–349, the disclosue of which is hereby incorporated by reference. Briefly, the radioimmunoassay for a compound or substance X may involve formation of a hapten comprising X, formation of an immunogen comprising the hapten of X, raising an antiserum comprising an antibody to X, and detecting X in a sample by use of said antibody and radiolabeled X.

Recently two radioimmunoassay techniques for atropine have been described, Fasth, A., Sollenberg, J. and Sorbo, B., "Production and Characterization of Antibodies to atropine", *Acta Pharm. Suec.*, 12:311 (1975); and Wurzburger, R., Miller, R., Boxenbaum, H., Spector, S., "Radioimmunoassay of atropine in plasma", *J. Pharmacol. Exp. Therap.*, 203:435 (1977), the latter of which (Wurzburger et al.) reaches the sensitivity necessary for pharmacokinetic studies. Both methods were shown to be stereoselective so that the pharmacologically inactive D-hyoscyamine was the principal enantiomer measured.

Virtanen et al., *Acta pharmacol. et toxicol.*, 47, 208–212 (1980) describe a radioimmunoassay for atropine and L-hyoscyamine alone. This work apparently relies upon the Wurzeburger et al. 1977 study for substantial experimental detail; it differs in that human serum albumin is substituted for bovine serum albumin. There is no disclosure as to determination of hapten to human serum albumin conjugation ratios for either atropine or L-hyoscyamine. This work does not describe the radioimmunoassay for L-hyoscyamine subsequent to administration of atropine to a human.

PURPOSE OF THE INVENTION

The purpose of this invention was to set up a specific and sensitive RIA for L-hyoscyamine in biological fluids that would allow the delineation of the pharmacokinetics of atropine antidote in humans. This new sensitive radioimmunoassay of L-hyoscyamine can be used to monitor drug levels in various clinical situations and thereby help alleviate unnecessary toxicity to the patient. A knowledge of the serum concentration of L-hyoscyamine is useful both in the study of atropine metabolism and in optimal therapeutic monitoring to avoid undue toxicity since similar doses of atropine may produce different responses in various population groups as white, black and mongoloid as well as different population subgroups. Currently available methods have lacked sufficient sensitivity to measure low levels of the drug present in plasma after useful therapeutic doses.

Whether these different responses to the drug are related to genetically influenced differences in atropine kinetics in certain patients can now be studied using the assay.

The radioimmunoassay of this invention has applicability to the civilian sector in view of the availability and usage of various therapeutic compositions containing atropine as earlier mentioned as well as military needs. As mentioned above, atropine is considered the antidote of choice for poisoning by cholinesterase inhibiting nerve agents tabun, sarin and soman. Atropine counteracts the effects of accumulation of neurotransmitter acetylcholine, which follows nerve agent exposure. The antidote does produce some unwanted side effects. It thus becomes essential to know how the drug might affect the performance of tasks by military personnel in a combat environment. Possible situations for drug misuse are: (1) personnel not exposed might inject themselves upon observing other troops using the antidote; (2) over-reaction resulting in the use of too many autoinjectors; (3) autoinjection as soon as a chemical agent alarm sounds (whether a false alarm or not) without waiting for the symptoms to appear; (4) prophylactic use of the antidote in the belief that the antidote will be beneficial by already being in the body; (5) because of misclassification or confusion as to the appropriate self-aid, atropine injectors can be used against agents other than nerve agents; (6) use of the antidote as a drug of abuse for mind-altering purposes.

Because of the possibility of inappropriate or untimely antidote usage in many military settings, a thorough description of the extent, magnitude, and time course of atropine's effects on military tasks is important. For example, atropine is known to exert a cycloplegic effect thus effecting near vision to the extent that one cannot write a message, plot coordinates on a map, or set fuses on rounds.

Other functional areas of interest include physical stress, neurological dysfunction, central disturbances and susceptibility toward self-injury.

Regarding physical stress, it is known that atropine hinders thermoregulation. This fact raises the question as to whether it predisposes men performing military tasks in a hot environment to heat exhaustion or heat stroke. As to neurological dysfunction, one is concerned with whether atropine causes muscular weakness or ataxia that is significantly detrimental to military tasks. Questions as to central disturbances involve hallucinations, inattentiveness or memory failure.

An additional important consideration is whether atropine-related side effects such as confusion and incoherence by a soldier in a combat situation unnecessarily endangers the soldier or others.

Therefor, it has become extremely important to measure the active form of the antidote L-hyoscyamine and to study the metabolism of the drug in different military situations using the antibody in a radioimmunoassay according to this invention.

SUMMARY OF THE INVENTION

A sensitive and specific radioimmunoassay has been developed for L-hyoscyamine resulting from atropine administration with which a concentration as low as 25 pg per ml using 0.1 ml of sample can be measured without the need for extraction. Specificity studies indicate that an antibody according to this invention has high specific recognition of L-hyoscyamine with only about 37% cross reaction with the D-hyoscyamine enantiomer of atropine. The antibody is produced from an immunogen having conjugated at least 42 and preferably 45 L-hyoscyamine-p-amino benzoic acid haptenic molecules per molecule of bovine serum albumin. An antibody according to this invention can be used with a dilution titer as high as 1:2000.

P-Aminobenzoic acid is initially diazotized following certain specific criteria and then coupled to L-hyoscyamine. It is not known at which position of the phenyl nucleus of the L-hyoscyamine molecule the diazotized PABA attaches. However, since the alkyl group on the phenyl ring is paradirecting, this would most probably be the site of attachment of the diazotized PABA. The resulting hapten is then conjugated to bovine serum album using the conventional carbodiimide reaction. The resulting immunogenic material is administered to rabbits to produce the anti-L-hyoscyamine antibodies. Antidotes raised can be used in the assay at a final antibody dilution of 1:2000. The assay can reliably detect as little as 25 picograms of L-hyoscyamine, and a 50% inhibition of the binding of the $^3$H-1-hyoscyamine ligand to the antibody can be attained with 500 picograms of L-hyoscyamine. The major metabolites of atropine do not cross-react with the antibody. It is possible to analyze serum samples directly by using the RIA of this invention, thereby eliminating tedious extraction procedure which is required by other methods. Using this RIA, the dispositon of L-hyoscyamine following intravenous administration of 1.0 mg of the drug to humans was examined. This invention is applicable to serum samples from a mammal other than a human such as the laboratory animals including monkey, sheep, goat, cat, guineau pig, rat, rabbit, dog, etc.

Ready comparison of the advantageous specificity of the present invention in comparison to that of the Wurzeburger et al. and Virtanen et al. radioimmunoassays is seen by reference to the following table:

| Specificity | Virtanen | Wurzeburger | Verma |
| --- | --- | --- | --- |
| L-hyoscyamine | 100% | 2.4%* | 100% |
| atropine | 100% | 100% | 37% |

*percentage of cross reactivity (0.8 mg/33 mg × 100%)

DETAILED DESCRIPTION OF THE INVENTION

The present invention concerns radioimmunoassays of L-hyoscyamine involving the use of an antibody raised in a white New Zealand rabbit from an immunogen having at least 42 haptenic modecules and preferably 45 haptenic molecules synthesized from diazotized p-aminobenzoic acid and L-hyoscyamine under acidic pH conditions. The levorotatory asymmetry of the L-hyoscyamine asymmetric carbon C* is believed to be retained in the hapten molecule. It is necessary that the diazotized p-aminobenzoic acid is synthesized from 1 part-by-weight sodium nitrite to 1–1.4 parts-by-weight p-aminobenzoic acid; preferably the ratio is 1 to about 1.1 respectively.

The immunogen of this invention is preferably administered to the rabbit at an initial dosage of at least 0.3 mg per rabbit and more preferably 0.4 mg per rabbit. Booster immunogen is preferably administered monthly at a dosage in the range of 0.17 mg to 0.25 mg per rabbit. More preferably, the dosage is 0.2 mg per rabbit per month for a period of at least three months. Practice of this invention can yield an antibody having a serum dilution titer as high as about 1 to 2000. The radioimmunoassay of L-hyoscyamine according to this invention is capable of detecting 25 picograms per milliliter of L-hyoscyamine using 0.1 milliliter of serum with a cross-reactivity of about 37% atropine.

The following detailed experiments are considered exemplary of facets of the invention and are directed to a preferred embodiment of the invention. Variations within the scope of the appended claims to this invention will be apparent to the skilled artisan.

Materials $^3$H-1-hyoscyamine, 4.1 Ci/mmol was supplied by the Nuclear Research Centre, Negev, Beer Sheva, Israel. Atropine, 1-hyoscyamine, dl-tropic acid, tropine, 1-scopolamine-HCl., dl-homatropine-HBr, p-aminobenzoic acid, bovine serum albumin and 1-ethyl-3-(3-dimethylaminopropyl) carbodiimide. HCl were obtained from Sigma Chemical Company, St. Louis, Mo.

Preparation of Immunogen

Figure 1:
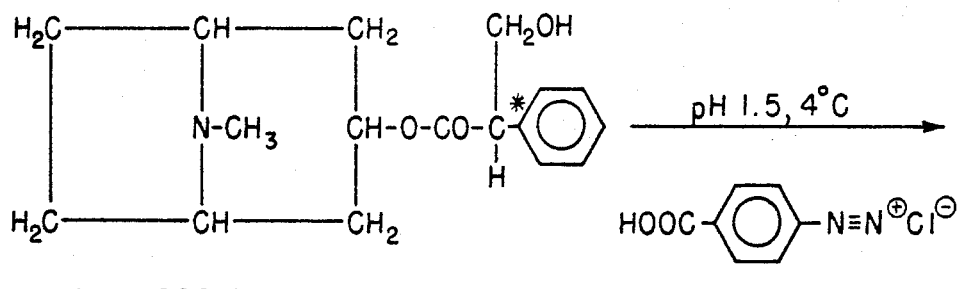
Figure 1:
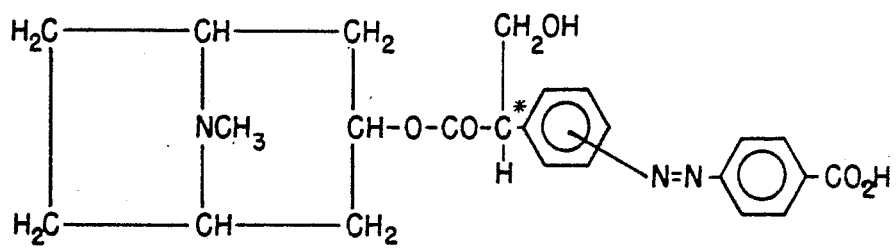
Figure 1:
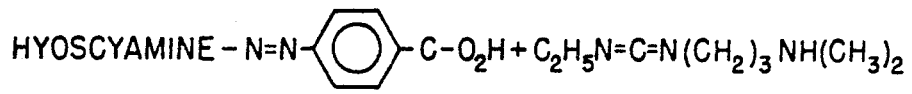
Figure 1:

P-aminobenzoic acid (PABA) was initially diazotized and then coupled to L-hyoscyamine. The hapten was then conjugated to bovine serum albumin (BSA) with the use of water soluble carbodiimide 1-ethyl-3-(3-dimethylaminopropy-1)-carbodimide HCl. The reaction sequence is illustrated in FIG. 1.

Preparation of L-Hyoscyamine Hapten

PABA 27.4 mg (0.2 mole) was dissolved in 3.0 ml 0.2 M HCl, and the solution was cooled to 0°–4° C. in an ice water bath. Sodium nitrite, 12.4 mg (0.18 mole) was dissolved in 2.0 ml of ice-cold water, and then added dropwise to the PABA solution at 4° C. with constant stirring. The mixture was stirred for another hour at 0° C. and checked with iodide-starch paper to assure that no excess of nitrous acid was present. L-Hyoscyamine, 57.8 mg (0.2 mmole) was dissolved in 2.0 ml of 0.1N HCl. The diazotized PABA solution was added dropwise to the solution of L-hyoscyamine while stirring and cooling in an ice water bath. The reaction was allowed to proceed in the dark for 4 hours at 4° C.

Conjugation to Bovine Serum Albumin

BSA 25 mg (0.0037 mmole) was added to the hapten solution and the pH was checked to verify that it was pH 6.00. Water soluble 1-ethyl-3-(3-dimethylaminopropyl)carbodiimide HCl, 100 mg was added and the reaction was allowed to proceed overnight at room temperature. The BSA-hyoscyamine immunogen was dialyzed against water for 24 hours at room temperature. The amount of substitution of hapten to BSA was determined by using radioactive L-hyoscyamine during the preparation of the immunogen. It was determined by conventional methods that there were 45 haptenic molecules per molecule of BSA.

Immunization Procedure

Four male New Zealand white rabbits were immunized with L-hyoscyamine-BSA immunogen. The rabbits initially received 0.4 mg of immunogen. The immunogen was dissolved in physiological saline and emulsified with an equal volume of complete Freund's adjuvant and mixture was injected intraperitoneally. Monthly injections were administered for the next 3 months using 0.2 mg of immunogen after preparing an emulsion with incomplete Freund's adjuvant. Blood was collected from the central ear artery one week after a booster injection. The blood was allowed to clot at room temperature and then centrifuged at 1500× g for 15 min; the separated serum was stored frozen until assayed for the presence of antibody.

Radioimmunoassy Procedure

The assay was carried out according to the protocol shown in Table 1. Tritiated L-hyoscyamine having specific activity 4.1 Ci/m mol was used as the tracer. The dilution of tracer, antiserum and cold standards was made with 0.1M Tris-HCl buffer containing 0.1% bovine gamma globulin Cohn fraction II, pH 7.5. The antiserum is used at a final dilution of 1:2000. Both standards and samples were always analyzed in duplicate.

The reagents were added to the assay tubes in the order shown in Table 1. After the addition of antiserum, the contents of the tubes were mixed and incubated for two hours at the room temperature. After the incubation, bound fraction was separated by adding saturated ammonium sulphate. The bound fraction was washed one time with 50% saturated ammonium sulphate. The bound fraction was dissolved in 1.0 ml distilled water, and the contents were mixed with 10 ml of acquasol scintillation fluid. The radioactivity was determined in a scintillation counter. Concentration of the drug in the unknown sample was determined according to conventional calculation from the standard curve of FIG. 3.

TABLE 1

PROTOCOL FOR RADIOIMMUNOASSAY PROCEDURE
Volume of Reagent added, μl

| REAGENT | Standard Tube | Zero Tube | Nonspecific Binding | Sample Tube |
|---|---|---|---|---|
| Assay buffer | 200 | 250 | 350 | 250 |
| Normal plasma | 100 | 100 | 100 | — |
| Standard | 50 | — | — | — |
| Sample | — | — | — | 100 |
| $^3$H - Tracer | 50 | 50 | 50 | 50 |
| Antiserum | 100 | 100 | — | 100 |
| Incubate 2 hr at 23 degrees C. | | | | |
| 100% Saturated Ammonium sulphate | 500 | 500 | 500 | 500 |
| 50% Saturated Ammonium sulphate | | 500 | 500 | 500 |

Validation of Radioimmunoassay of L-hyoscyamine Antiserum Production

Figure 2:
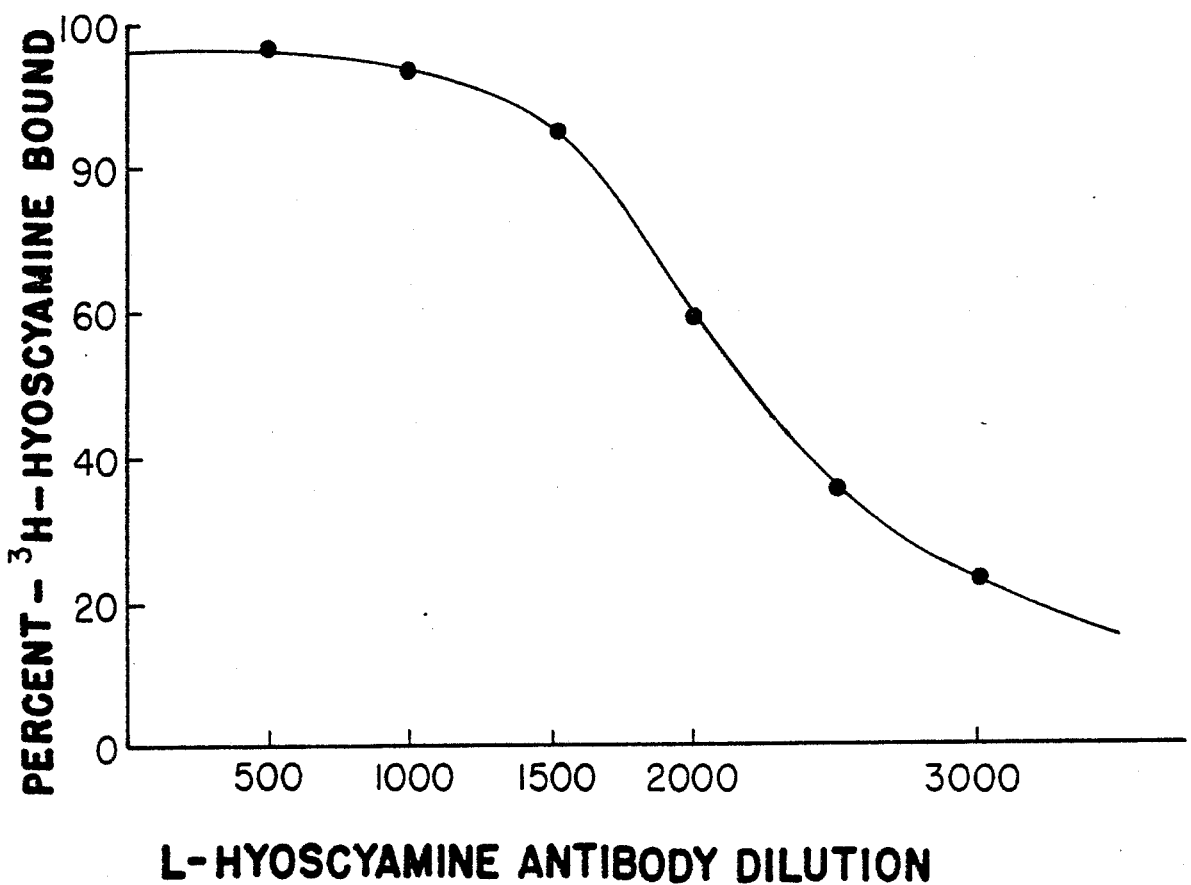

The rabbits were first bled 8 weeks after the initiation of the immunization procedure and antibodies were detectable at this time. The L-hyoscyamine conjugate proved to be immunogenic in all the immunized rabbits. After the 5th booster injection, the titer (defined as the final dilution of the antiserum needed to bind 50% of the added $^3$H-Hyoscyamine) of the antisera was about 1:2000 (FIG. 2). This antiserum was used in work further described hereinbelow. Currently by practice of this invention antisera sufficient for millions of clinical tests is available. If needed it can be produced at mass scale.

Radioimmunoassay Procedure

Figure 3:
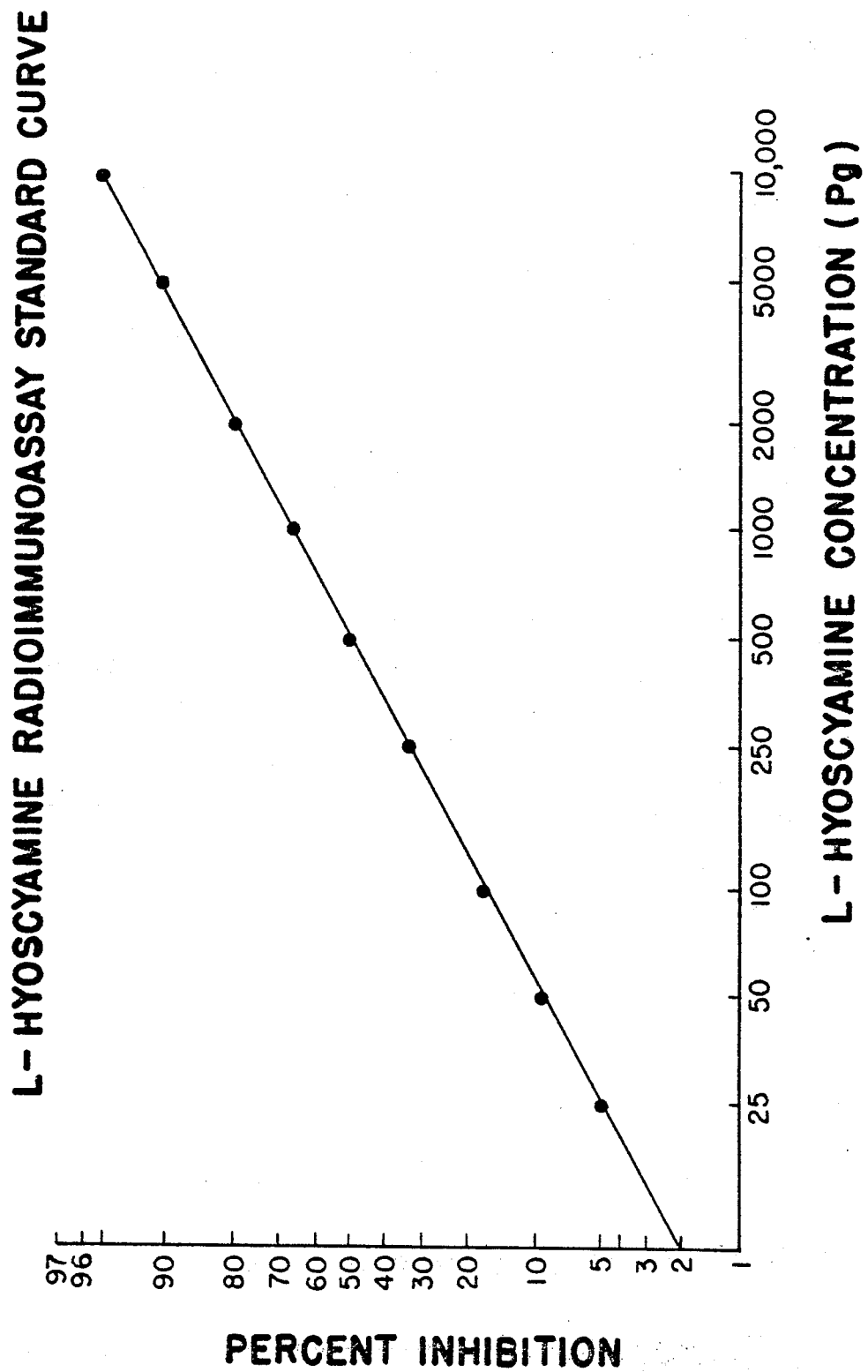

FIG. 3 shows a typical L-Hyoscyamine standard curve. About 25 pg/ml of L-hyoscyamine can be distinguished from zero and the useful range of the curve extends up to 10 ng per assay tube. Addition 100 l of normal human plasma or serum had no effect on either the nonspecific binding or the standard curve indicating lack of interfering substances in the body.

Metabolities and analogs of atropine were tested, up to 500 g, for cross-reactivity. The results obtained are presented in Table 2. L-hyoscyamine produced a 50% inhibition of binding of $^3$H-L-hyoscyamine to the antibody at a concentration of 500 pg. The only compounds recognized by the antibody to any extent were atropine, and homatropine. The cross-reactivity of the antibody with atropine is expected since it contains 50% L-hyoscyamine. The atropine hydrolysis products, tropic acid and tropine did not cross-react with the antibody. Since L-hyoscyamine inhibits the action of acetylcholine, this compound was also checked for cross-reactivity; it too was not recognized by the antibody.

TABLE 2

| SPECIFICITY OF ANTISERUM | |
|---|---|
| Compound | % Cross-reactivity |
| L-Hyoscyamine | 100 |
| Atropine | 30 |

TABLE 2-continued

| SPECIFICITY OF ANTISERUM | |
|---|---|
| Compound | % Cross-reactivity |
| Scopolamine | 0 |
| Homatropine | 0.2 |
| Tropine | 0 |
| Tropic Acid | 0 |
| Acetylcholine | 0 |

Regarding laboratory quality control, recovery was determined by adding 50–300 pg of L-hyoscyamine to normal human plasma. Recovery by this method is in excellent agreement with the added quantities of L-hyoscyamine in normal human plasma (Table 3). Inter-assay and intra-assay coefficient of variation were always less than 10%.

Non-specific binding was only 3–4% and there were no blank effects by several individual normal serums tested.

| Recovery of L-Hyoscyamine added to the normal plasma* | |
|---|---|
| L-Hyoscyamine Added (pg) | Recovery % |
| 50 | 92.5 |
| 100 | 96.3 |
| 200 | 102.2 |
| 300 | 101.5 |

*L-Hyoscyamine was added to the normal plasma and sample were processed as described. Percent recovery was calculated from the mean value of the measurements, 10 assay tubes at each dose.

Human Studies

The usefulness of the RIA method of this invention in pharmacokinetics work and monitoring the drug in a patient was studied by determining L-hyoscyamine concentrations in serial (0–8 hrs.) serum samples from 6 healthy male volunteers who were given 1.0 mg or 2 mg of atropine, in the form of its sulfate salt, intravenously. Results are shown in Table 4.

TABLE 4

| Serum levels (pg/ml) of six healthy males after intravenous administration of atropine sulfate. | | | | | |
|---|---|---|---|---|---|
| Time After Administration | HUMAN SUBJECTS | | | | |
| (Min) | *A | *B | *C | *D | +E | +F |
| 0 | 0 | 0 | 0 | 0 | 0 | 0 |
| 2 | 1300 | 4600 | 4600 | 1600 | 10800 | 10400 |
| 4 | 800 | 2800 | 1300 | 900 | 9500 | 10000 |
| 8 | 600 | 1600 | 950 | 740 | 5800 | 9600 |
| 12 | 500 | — | 600 | 680 | 5800 | 8000 |
| 16 | 460 | 1200 | 560 | 900 | 5600 | 6400 |
| 20 | 460 | 720 | 600 | 600 | 5600 | 5000 |
| 30 | 560 | 720 | 760 | 600 | 5400 | 3800 |
| 45 | 600 | 600 | 540 | 500 | — | — |
| 60 | 420 | 560 | 500 | 500 | 5000 | 3200 |
| 120 | 380 | 460 | 360 | 420 | 4800 | 2700 |
| 180 | 370 | 360 | 350 | 270 | 4300 | 1600 |
| 240 | 270 | 360 | 280 | 180 | 3200 | 1200 |
| 360 | 200 | — | — | — | — | — |
| 480 | 180 | 180 | 220 | 120 | 1300 | 1200 |

*One mg of atropine sulfate was administered.
+2.0 mg of atropine sulfate was administered.

Figure 4:
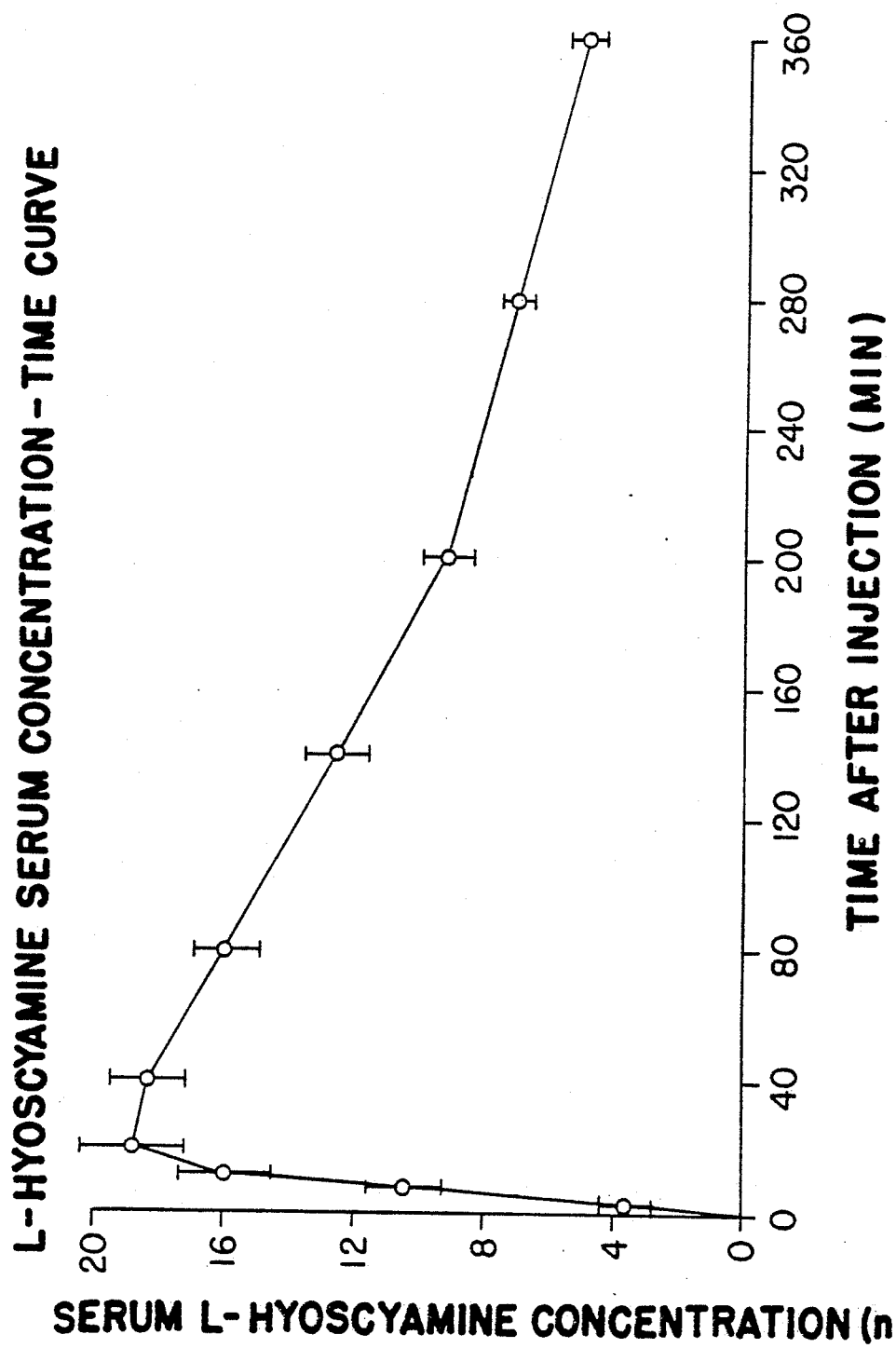

The RIA was then applied to the determination of l-hyoscyamine in human serum following intramuscular injection of 1.0 mg atropine sulphate as shown in FIG. 4. The main peak serum level of 19 mmoles/l was attained within 20 minutes, then fell to give a steady decline curve after 40 minutes. Serum levels of l-hyoscyamine had fallen to approximately 50% levels after 3 hours.

I claim:

1. An immunogen for the production of an antibody to L-hyoscyamine antigen produced by the process comprising:
   (a) allowing L-hyoscyamine to react with diazotized p-aminobenzoic acid at an acidic pH to produce a hapten having the structural formula

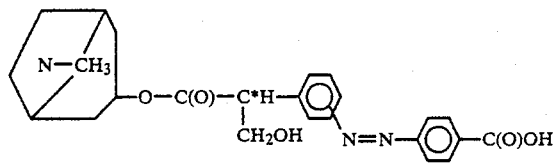

wherein the levatory asymmetry of the asymmetric carbon C* is retained, said diazotized p-aminobenzoic acid synthesized from 1 part-by-weight sodium nitrite to 1–1.4 parts-by-weight p-aminobenzoic acid; and
   (b) allowing said hapten of L-hyoscyamine to conjugate with bovine serum albumin to form L-hyoscyamine-bovine serum albumin immunogen, said immunogen having conjugated at least 42 hapten molecules per molecule of bovine serum albumin.

2. An immunogen for the production of antibody to the L-hyoscyamine antigen produced by a process comprising:
   (a) allowing L-hyoscyamine to react with diazotized p-aminobenzoic acid to form the hapten of L-hyoscyamine according to claim 1; and
   (b) allowing said hapten of L-hyoscyamine to conjugate with bovine serum albumin to form L-hyoscyamine-bovine serum albumin immunogen, said immunogen having conjugated at least 42 hapten molecules per molecule of bovine serum allumin.

3. An immunogen produced by the process of claim 1 wherein the diazotized p-aminobenzoic acid is synthesized from 1 part-by-weight sodium nitrite to about 1.1 parts-by-weight p-amino benzoic acid.

4. An immunogen according to claim 3 having 45 hapten modecules per molecule of bovine serum albumin.

5. An antibody for the radioimmunoassay detection of L-hyoscyamine produced by the process comprising administering to a New Zealand White rabbit the immunogen according to claim 1, then harvesting plasma containing said antibody from a blood sample withdrawn from the immunized rabbit.

6. An antibody according to claim 5 wherein said immunogen is administered to said rabbit at an initial dosage of at least 0.3 mg per rabbit.

7. An antibody according to claim 6 wherein the initial dosage is 0.4 mg per rabbit.

8. An antibody according to claim 6 wherein the administration of immunogen subsequent to the initial dosage is monthly at a dosage in the range of 0.17 mg–0.25 mg per rabbit.

9. An antibody according to claim 8 wherein the dosage is 0.2 mg per rabbit per month for a period of at least three months.

10. An antibody according to claim 5 having a serum dilution titer of about 1:2000.

11. A method for the radioimmunoassay of L-hyoscyamine in a mammal to which atropine has been administered comprising allowing a blood sample from said mammal to react with a quantity of serum containing the antibody according to claim 5, and detecting said L-hyoscyamine in the presence of atropine.

12. A method for the radioimmunoassay of L-hyoscyamine according to claim 11 wherein the mammal is a human.

13. A method for the radioimmunoassay of L-hyoscyamine according to claim 12 sufficiently sensitive to detect 25 pg per ml of L-hyoscyamine using 0.1 ml of serum with a cross-reactivity of about 37% atropine.

* * * * *

UNITED STATES PATENT AND TRADEMARK OFFICE
CERTIFICATE OF CORRECTION

Page 1 of 2

PATENT NO. : 4,591,573
DATED : May 27, 1986
INVENTOR(S) : Pritam S. Verma

It is certified that error appears in the above-identified patent and that said Letters Patent is hereby corrected as shown below:

On page 1, immediately following the "Abstract", "13 Claims" should be --12 Claims--.

Column 10, lines 29 through 39 (Claim 2) should be cancelled.

Column 10, line 40, "3." should be --2.--.

Column 10, line 44, "4." should be --3.--, and "claim 3" should be --claim 2--.

Column 10, line 47, "5." should be --4.--.

Column 10, line 53, "6." should be --5.--, and "claim 5" should be --claim 4--.

Column 10, line 56, "7." should be --6.--, and "claim 6" should be --claim 5--.

Column 10, line 58, "8." should be --7.--, and "claim 6" should be --claim 5--.

Column 10, line 62, "9." should be --8.--, and "claim 8" should be --claim 7--.

Column 10, line 65, "10." should be --9.--, and "claim 5" should be --claim 4--.

UNITED STATES PATENT AND TRADEMARK OFFICE
CERTIFICATE OF CORRECTION

PATENT NO. : 4,591,573

DATED : May 27, 1986

INVENTOR(S) : Pritam S. Verma

It is certified that error appears in the above-identified patent and that said Letters Patent is hereby corrected as shown below:

Column 10, line 67, "11." should be --10--.

Column 11, line 3, "Claim 5" should be --Claim 4--.

Column 11, line 5, "12." should be --11.--.

Column 12, line 1, "Claim 11" should be --Claim 10--.

Column 12, line 3, "13." should be --12--.

Column 12, line 4, "Claim 12" should be --Claim 11--.

Signed and Sealed this

Seventh Day of April, 1987

Attest:

Attesting Officer

DONALD J. QUIGG

Commissioner of Patents and Trademarks